United States Patent [19]

Kapur et al.

[11] Patent Number: 4,576,754

[45] Date of Patent: Mar. 18, 1986

[54] PREPARATION OF 6,6-DIBROMO-PENICILLANIC ACID-1,1-DIOXIDE

[75] Inventors: Jagdish C. Kapur; Herman P. Fasel, both of Delft, Netherlands

[73] Assignee: Gist-Brocades N.V., Delft, Netherlands

[21] Appl. No.: 659,089

[22] Filed: Oct. 10, 1984

[30] Foreign Application Priority Data

Oct. 18, 1983 [EP] European Pat. Off. ........ 83201496.3

[51] Int. Cl.⁴ .................. C07D 499/00; A61K 31/425
[52] U.S. Cl. ............................................ 260/245.2 R
[58] Field of Search ................ 260/245.2 R, 245.2 T; 424/270; 514/192, 194

[56] References Cited

U.S. PATENT DOCUMENTS

| 4,397,783 | 8/1983 | Kellogg | 260/245.2 R |
| 4,420,426 | 12/1983 | Moore | 260/245.2 R |
| 4,432,970 | 2/1984 | Kellogg | 260/245.2 R |

FOREIGN PATENT DOCUMENTS

| 0030771 | 4/1983 | European Pat. Off. . |
| 0092286 | 10/1983 | European Pat. Off. . |
| 0093465 | 11/1983 | European Pat. Off. . |
| 2000138A | 1/1979 | United Kingdom . |
| 2045755A | 11/1980 | United Kingdom . |

OTHER PUBLICATIONS

*Jour. of Org. Chemistry,* vol. 27, pp. 1693–2710, (1962).
*Jour. of the Chem. Soc.,* 1821–2832 (1969) (London).

*Primary Examiner*—Nicholas S. Rizzo
*Attorney, Agent, or Firm*—Bierman, Peroff & Muserlian

[57] ABSTRACT

In a process for the preparation of 6,6-dibromo-penicillanic acid-1,1-dioxide comprising reacting 6β-aminopenicillanic acid-1,1-dioxide with a nitrosating agent in the presence of bromine and an inorganic acid or strong organic acid, the improvement comprising effecting the reaction in the presence of an alcohol resulting in a high purity product.

14 Claims, No Drawings

PREPARATION OF 6,6-DIBROMO-PENICILLANIC ACID-1,1-DIOXIDE

STATE OF THE ART

The presumed association between the resistance of certain bacteria to $\beta$-lactam antibiotics and the capability of these bacteria to produce and secret $\beta$-lactamases has led to an intensive search for $\beta$-lactamase inhibitors. Dutch patent application No. 7806126 teaches that penicillanic acid-1,1-dioxide and the salts and esters thereof have useful pharmacological properties, for example as effective inhibitors of several types of $\beta$-lactamases present in various kinds of bacteria. In the said Dutch application, a process is described for the preparation of penicillanic acid-1,1-dioxide and salts and esters thereof by oxidation of penicillanic acid.

Another process for the preparation of penicillanic acid-1,1-dioxide in described in Dutch patent application No. 8001285 wherein penicillanic acid-1,1-dioxide is prepared by diazotization-bromination of 6-amino-penicillanic acid followed by oxidation of the formed 6,6-dibromo-penicillanic acid into 6,6-dibromo-penicillanic acid-1,1-dioxide and dehalogenation of the latter compound.

In European patent application No. 83200541, a process is described for the preparation of a mixture of 6,6-dibromo-penicillanic acid-1,1-dioxide and 6$\alpha$-bromo-penicillanic acid-1,1-dioxide by diazotization-bromination of 6-amino-penicillanic acid-1,1-dioxide. The relative amount of dibromo compound in the mixture usually varies from 80–90% and the relative amount of monobromo compound varies from 10–20%. The mixture of the bromo compounds thus prepared can be reduced into penicillanic acid-1,1-dioxide for instance by the method described in European patent application No. 83200542.

In said European patent application No. 83200541, the mixture of 6,6-dibromo-penicillanic acid-1,1-dioxide and 6$\alpha$-bromo-penicillanic acid-1,1-dioxide is prepared by reaction of 6-amino-penicillanic acid-1,1-dioxide with a nitrosating agent in the presence of hydrogen bromide and bromine. The reaction is performed at a temperature between $-20°$ C. and 30° C. with at least an equimolar amount of a nitrosating agent in the presence of 1 to 5 equivalents of a strong inorganic or organic acid in solution or suspension of a mixture of water and a partly or completely water-miscible organic solvent medium, the amount of water present being from 1 to 20% by volume and containing hydrogen bromide and bromine in at least equimolar amounts. Optionally, an auxiliary agent which facilitates the bromination of the diazotized intermediate in an amount varying from 10% to at least an equimolar amount of the amino-penicillanic acid-1,1-dioxide starting material can be used. The maximum yield of 6,6-dibromo-penicillanic acid-1,1-dioxide and 6$\alpha$-bromo-penicillanic acid-1,1-dioxide in the examples of the above mentioned European patent application calculated on the starting 6-amino-penicillanic acid-1,1-dioxide did not exceed 70% in spite of the extensive disclosure.

OBJECTS OF THE INVENTION

It is an object of the invention to provide an improved process for preparing 6,6-dibromo-penicillanic acid-1,1-dioxide in high purity.

It is a further object of the invention to provide a process for preparing 6,6-dibromo-penicillanic acid-1,1-dioxide with a simple recovery procedure.

These and other objects and advantages of the invention will become obvious from the following detailed description.

THE INVENTION

The novel process of the invention for the preparation of 6,6-dibromo-penicillanic acid-1,1-dioxide comprises reacting 6$\beta$-amino-penicillanic acid-1,1-dioxide with a nitrosating agent in the presence of bromine and a strong inorganic or organic acid and the further presence of an alcohol. The process results in pure 6,6-dibromo-penicillanic acid-1,1-dioxide being prepared in a considerably higher yield than that described in the European application No. 83200541 by the addition of a small amount of an alcohol to the reaction mixture of the diazotization-bromination reaction of 6-amino-penicillanic acid-1,1-dioxide.

When using the process of the present invention, it is possible to prepare pure 6,6-dibromo-penicillanic acid-1,1-dioxide in a yield of 90% and in comparison with the process described in European patent application No. 83200541, a relative improvement of the amount of bromo compounds of about 30% is reached. This means that the cost price of the bromo compounds as prepared by the older process will be 30% higher than the cost price of the dibromo compound as prepared by the process of the present invention and the improvement of the yield is illustrated for instance by Examples 3 and 6 of the present application. Keeping all the other reaction conditions the same, the yield of 6,6-dibromo-penicillanic acid-1,1-dioxide improves from 53 to 90% by the addition of a small amount of methanol.

Furthermore, the recovery procedure in the present process is usually simpler than in the process described in European patent application No. 83200541. In that application, it is necessary to remove the water-miscible solvent by azeotropic destillation or by evaporation in vacuo since otherwise the extraction of the product from the aqueous layer would give problems. As the reaction of the present invention can be performed in methylene chloride, it is not necessary to remove the water-miscible solvent which is an important feature in a commercial scale chemical process.

Another advantage of the present application is that 6,6-dibromo-penicillanic acid-1,1-dioxide of a high purity is obtained and the ultimately desired product, i.e. penicillanic acid-1,1-dioxide, will therefore also have a high purity which is an important feature of compounds to be used for the preparation of pharmaceutical compositions. Also the fact that the process of the present invention results in pure 6,6-dibromo-penicillanic acid-1,1-dioxide and is not mixed with an amount of 6$\alpha$-bromo-penicillanic acid-1,1-dioxide has a positive influence on the quantity of the end product.

6,6-dibromo-penicillanic acid-1,1-dioxide can be converted into the desired acid-1,1-dioxide according to known methods such as the process described in British patent application No. 2,045,755 and the process described in European patent application No. 83200542.

The reaction is carried out by addition of bromine, aqueous hydrobromic acid and the alcohol to a solution or suspension of 6-amino-penicillanic acid-1,1-dioxide acid in an organic solvent followed by the addition of the nitrosating agent. After stirring for 5 minutes to 1 hour, an eventual excess of bromine is removed for instance by addition of an aqueous solution of sodium bisulfite. Extraction with an organic solvent, drying in the usual way and evaporation of the solvent results in the desired 6,6-dibromo-penicillanic acid-1,1-dioxide.

Examples of alcohols which can be used in the process of the invention are alkanols of 1 to 10 carbon atoms such as methanol, ethanol, propanol, isopropanol, t-butyl alcohol, pentanol, hexanol; cycloalkanols such as cyclohexanol; aromatic alcohols such as benzyl alcohol; and polyols such as 1,2-propanediol and glycerol. However, the scope of the present invention is not limited to the above mentioned alcohols, but can also be extended to other alcohols, preferably a $C_1$–$C_4$ alkanol or $C_1$–$C_4$ alkenediol. Preferably methanol is used and the amount of alcohol may vary between 1 and 10 equivalents calculated on the starting 6-amino-penicillanic acid-1,1-dioxide.

Preferably 2-6 equivalents of the alcohol are used, more preferably 4 equivalents. Examples of inorganic acids and strong organic acids are hydrobromic acid, hydrochloric acid, sulfuric acid, phosphoric acid, aminosulfonic acid, chloroacetic acid, dichloroacetic acid and trifluoroacetic acid. Preferably, hydrobromic acid is used.

Suitable organic solvents in which the reaction can be carried out are inert organic solvents, for example methylene chloride, chloroform and acetonitrile can be used and preferably methylene chloride is used. The reaction can be carried out at a temperature between −20° and 30° C., preferably between −10° and 15° C. The nitrosating agent to be used in the reaction can be an alkali metal nitrite or an alkyl nitrite. Preferably sodium nitrite is used.

The starting 6-amino-penicillanic acid-1,1-dioxide can be prepared as described in European Pat. No. 0030771.

In the following examples there are describes several preferred embodiments to illustrate the invention. However, it is to be understood that the invention is not intended to be limited to the specific embodiments.

Alcohol-free dichloromethane was used in all the examples and the purity of 6,6-dibromo-penicillanic acid-1,1-dioxide was determined through 60 MHz-NMR spectra using either maleic acid as the reference in dimethylsulfoxide-$d_6$ or 2,6-dichloroacetophenone as the reference in acetone-$d_6$, unless otherwise stated.

EXAMPLE 1

To a suspension of 6.2 g of 6β-amino-penicillanic acid-1,1-dioxide (purity by HPLC 90%; 22.5 mmol) in 75 ml of dichloromethane cooled to about −5° to −0° C. was added a solution of 6.0 g (37.5 mmol) of bromine in 25 ml of dichloromethane, 7.1 ml (64.0 mmol) of hydrobromic acid and 2 ml (49.4 mmol) of methanol. 2.05 g (29.7 mmol) of sodium nitrite were added portionwise over a period of 10–15 minutes and during the addition of sodium nitrite, the reaction mixture was maintained at 0° to 5° C. The contents were stirred for another 30 minutes at the same temperature and then a solution of 35 ml of 10% aqueous sodium bisulfite was added dropwise at 0° to 5° C. till the bromine color was discharged and the reaction mixture was extracted 4 times with 200 ml of chloroform. The combined extracts were washed with brine (2 times 100 ml) and dried over anhydrous magnesium sulfate. The solvent was evaporated and the residue was washed with n-hexane and dried under reduced pressure to obtain 7.29 g of 6,6-dibromo-penicillanic acid-1,1-dioxide with a purity of 99.1% and a yield of 82.2%.

IR Spectrum (KBr): 2700–3300, 1811, 1740, 1333 $cm^{-1}$.

NMR (DMSO-$d_6$): δ-values in ppm, TMS, 60 MHz): 1.43 (s, 3H, $CH_3$), 1.53 (s, 3H, $CH_3$), 4.72 (s, 1H, $C^3H$), 6.02 (s, 1H, $C^5H$). The purity was determined through 60 MHz NMR spectroscopy using maleic acid as the reference.

EXAMPLE 2

The reaction was carried out as described in Example 1, but the amount of methanol used was 3 ml (74.1 mmol) instead of 2 ml. The isolated yield of 6,6-dibromo-penicillanic acid-1,1-dioxide was 7.93 g with a purity of 98.5% giving a yield of 88.9%.

EXAMPLE 3

The reaction was carried out as described in Example 1, but the amount of methanol used was 4 ml (98.75 mmol) instead of 2 ml. The isolated yield of 6,6-dibromo-penicillanic acid-1,1-dioxide was 7.98 g with a purity of 99.1% giving a yield of 89.9%.

EXAMPLE 4

The reaction was carried out as described in Example 1, but the amount of methanol used was 5 ml (123.4 mmol) instead of 2 ml. The isolated yield of 6,6-dibromo-penicillanic acid-1,1- was 8.09 g with a purity of 90.9% giving a yield of 83.6%.

EXAMPLE 5

The reaction was carried out as described in Example 1, but the amount of methanol used was 6 ml (148.1 mmol) instead of 2 ml. The isolated yield of 6,6-dibromo-penicillanic acid-1,1-dioxide was 8.23 g with a purity of 92.6% giving a yield of 86.7%.

EXAMPLE 6

The reaction was performed as described in Example 1, but the amount of hydrobromic acid was 7.46 ml (67 mmol) and no methanol was used. The isolated yield of 6,6-dibromo-penicillanic acid-1,1-dioxide was 4.72 g with a purity of 98.8% giving a yield of 53.1%.

EXAMPLE 7

The reaction was carried out as described in Example 6, but the amount of methanol used was 0.1 ml (2.47 mmol). The isolated yield of 6,6-dibromo-penicillanic acid-1,1-dioxide was 5.1 g with a purity of 97.15% giving a yield of 57.2%.

EXAMPLE 8

The reaction was carried out as described in Example 6, but the amount of methanol used was 0.4 ml (9.9 mmol). The isolated yield of 6,6-dibromo-penicillanic acid-1,1-dioxide was 5.76 g with a purity of 94.85% giving a yield of 62.3%.

EXAMPLE 9

The reaction was carried out as described in Example 6, but the amount of methanol used was 1 ml (24.7 mmol). The isolated yield of 6,6-dibromo-penicillanic acid-1,1-dioxide was 7.08 g with a purity of 99.4% giving a yield of 80.1%.

EXAMPLE 10

The reaction was carried out as described in Example 6, but the amount of methanol used was 2 ml (49.4 mmol). The isolated yield of 6,6-dibromo-penicillanic acid-1,1-dioxide was 7.72 g with a purity of 96.9% giving a yield of 85.2%.

EXAMPLE 11

The reaction was carried out as described in Example 1, but the amount of methanol used was 3 ml (74.06 mmol). The isolated yield of 6,6-dibromo-penicillanic acid-1,1-dioxide was 7.54 g with a purity of 98.6% giving a yield of 84.6%.

EXAMPLE 12

The reaction was carried out as described in Example 6, but the amount of methanol used was 4 ml (98.8 mmol). The isolated yield of 6,6-dibromo-penicillanic acid-1,1-dioxide was 8.00 g with a purity of 96.97% giving a yield of 88.3%.

EXAMPLE 13

The reaction was carried out as described in Example 6, but the amount of methanol used was 5 ml (123.4 mmol). The isolated yield of 6,6-dibromo-penicillanic acid-1,1-dioxide was 8.17 g with a purity of 95.7% giving a yield of 89%.

EXAMPLE 14

The reaction was carried out as described in Example 6, but the amount of methanol used was 6 ml (148.1 mmol). The isolated yield of 6,6-dibromo-penicillanic acid-1,1-dioxide was 8.01 g with a purity of 97.7% giving a yield of 89%.

EXAMPLE 15

The reaction was carried out as described in Example 1, but the amount of methanol used was 7 ml (172.8 mmol). The isolated yield of 6,6-dibromo-penicillanic acid-1,1-dioxide was 7.10 g with a purity of 94.3% giving a yield of 77%. The mother liquor from the isolated product was concentrated in vacuum and dried. NMR analysis of the residue showed that it contained 0.4 g of 6,6-dibromo-penicillanic acid-1,1-dioxide or 5.3% giving a total yield of 82.3%.

EXAMPLE 16

The reaction was carried out as described in Example 6, but 75 ml of methanol were used as solvent instead of methylene chloride. 5.99 g (37.5 mmol) of bromine were added as a solution in 125 ml of methanol. After neutralization of excess bromine, the extraction with chloroform were carried out at a pH of 3.5 and the isolated yield of the crude product was 5.83 g. The NMR spectrum of the crude product showed the presence of 6,6-dibromo-penicillanic acid-1,1-dioxide, 6α-bromo-penicillanic acid-1,1-dioxide and 6-bromo-6-methoxy-penicillanic acid-1,1-dioxide in a molar ratio of 2.8; 6.9; 9.5, respectively and cleaved product(s). The amount of these compounds was determined by 60 MHz NMR spectroscopy using maleic acid as the reference (yield=13.05%; 26.95% and 41.05% respectively), thus giving a yield of 8.7% of 6,6-dibromo-penicillanic acid-1,1-dioxide 22.4% of 6α-bromo-penicillanic acid-1,1-dioxide and 31.1% of 6-bromo-6-methoxy-penicillanic acid-1,1-dioxide.

The structure of 6-bromo-6α-methoxy-penicillanic acid-1,1-dioxide was confirmed by identification of the corresponding methyl ester as follows: 3 g of the above crude bromo-acids were taken up in ether and the solution was cooled to 0° C. Then diazomethane (solution in ether) was added till the yellow color persisted and the mixture was stirred at the same temperature for 45 minutes. Excess diazomethane was destroyed by addition of glacial acetic acid and the solvent was removed under reduced pressure. The resulting product was taken up in 60 ml of ethyl acetate and 10 ml of water were added and the solution was cooled to about 0° C. Then with 1N NaOH, the pH was adjusted to 7.0. The organic layer was separated, washed with brine, dried over anhydrous magnesium sulfate and the solvent was removed under reduced pressure to obtain 2.59 g of a thick oily liquid containing a mixture of the methyl esters of 6,6-dibromo-penicillanic acid-1,1-dioxide, 6α-bromo-penicillanic acid-1,1-dioxide and 6-bromo-6α-methoxy-penicillanic acid-1,1-dioxide as the main products. 2.2 g of this mixture were chromatographed by means of HPLC (Merck Column C) using ethyl acetate-n-hexane (1:3) as the eluent. The fractions containing the methyl ester of 6-bromo-6α-methoxy-penicillanic acid-1,1-dioxide were collected and evaporated under reduced pressure to obtain 0.889 g of a solid product.

IR(CHCl$_3$): 1810, 1760, 1339 cm$^{-1}$.

NMR(CDCl$_3$): δ-values in ppm. TMS, 60 MHz): 1.42 (s, 3H), 1.63 (s, 3H), 3.68 (s, 3H), 3.88 (s, 3H), 4.53 (s, 1H), 4.30 (s, 1H).

Mass spectrum m/e: 355, 357.

EXAMPLE 17

The reaction was carried out as described in Example 1, but the amount of hydrogen bromide used was 7.83 ml (70.4 mmol) The isolated yield of 6,6-dibromo-penicillanic acid-1,1-dioxide was 7.76 g with a purity of 98.1% giving a yield of 86.6%.

EXAMPLE 18

The reaction was carried out as described in Example 17, but the amount of methanol used was 3 ml (74.1 mmol). The isolated yield of 6,6-dibromo-penicillanic acid-1,1-dioxide was 7.73 g with a purity of 93.75% giving a yield of 82.5%.

EXAMPLE 19

The reaction was carried out as described in Example 17, but the amount of methanol used was 4 ml (98.8 mmol). The isolated yield of 6,6-dibromo-penicillanic acid-1,1-dioxide was 7.96 g with a purity of 99.8% giving a yield of 90.3%.

EXAMPLE 20

The reaction was carried out as described in Example 17, but the amount of methanol used was 5 ml (123.4 mmol). The isolated yield of 6,6-dibromo-penicillanic acid-1,1-dioxide was 8.01 g with a purity of 96.65% giving a yield of 88.1%.

EXAMPLE 21

The reaction was carried out as described in Example 17, but the amount of methanol used was 6 ml (148.13 mmol). The isolated yield of 6,6-dibromo-penicillanic acid-1,1-dioxide was 8.09 g with a purity of 96.9% giving a yield of 89.1%.

EXAMPLE 22

The reaction was carried out as described in Example 1, but the amount of methanol used was 4 ml (98.8 mmol) and the amount of hydrobromic acid was 1 ml (8.98 mmol). The isolated yield of 6,6-dibromo-penicillanic acid-1,1-dioxide was 5.70 g with a purity of 83.6% giving a yield of 54.8%.

EXAMPLE 23

The reaction was carried out as described in Example 22, but the amount of hydrobromic acid was 2 ml (17.96 mmol). The isolated yield of 6,6-dibromo-penicillanic acid-1,1-dioxide was 7.43 g with a purity of 87.95% giving a yield of 75.2%.

EXAMPLE 24

The reaction was carried out as described in Example 22, but the amount of hydrobromic acid was 3 ml (26.94 mmol). The isolated yield of 6,6-dibromo-penicillanic acid-1,1-dioxide was 7.63 g with a purity of 89.55% giving a yield of 78.6%.

EXAMPLE 25

The reaction was carried out as described in Example 22, but the amount of hydrobromic acid was 4.63 ml (41.56 mmol). The isolated yield of 6,6-dibromo-penicillanic acid-1,1-dioxide was 7.81 g with a purity of 93.95% giving a yield of 84.4%.

EXAMPLE 26

The reactin was carried out as described in Example 22, but the amount of hydrobromic acid was 5.3 ml (47.56 mmol). The isolated yield of 6,6-dibromo-penicillanic acid-1,1-dioxide was 7.77 g with a purity of 95.7% giving a yield of 85.6%.

EXAMPLE 27

The reaction was carried out as described in Example 22, but the amount of hydrobromic acid was 6.4 ml (57.56 mmol). The isolated yield of 6,6-dibromo-penicillanic acid-1,1-dioxide was 7.84 g with a purity of 95.2% giving a yield of 85%.

EXAMPLE 28

The reaction was carried out as described in Example 22, but the amount of hydrobromic acid was 9.17 ml (82.35 mmol). The isolated yield of 6,6-dibromo-penicillanic acid-1,1-dioxide was 7.79 g with a purity of 97.35% giving a yield of 86.1%.

EXAMPLE 29

Using the procedure of Example 1, 31 g purity by HPLC=90%; 112.5 mmol) of 6$\beta$-amino-penicillanic acid-1,1-dioxide, (375 ml of dichloromethane, 30 g (187.5 mmol) of bromine in 125 ml of dichloromethane, (35.4 ml 318 mmol) of hydrobromic acid, 20 ml 493.8 mmol of methanol, (10.25 g 148.5 mmol) of sodium nitrite, and 18 g of sodium metabisulfite in 180 ml water and brine (2×500 ml) were reacted and the isolated yield of 6,6-dibromo-penicillanic acid-1,1-dioxide was 39.65 g with a purity of 99.3% giving a yield of 89.6%.

EXAMPLE 30

The reaction was carried out as described in Example 1, but the amount of methanol used was 4 ml (98.75 mmol), the amount of hydrobromic acid was 7.46 ml (67 mmol) and 3.95 ml (29.7 mmol) of pentylnitrite were used instead of sodium nitrite. The isolated yield of 6,6-dibromo-penicillanic acid-1,1-dioxide was 7.0 g with a purity of 93.75% giving a yield of 75.5%.

EXAMPLE 31

The reaction was carried out as described in Example 12, but the amount of 6$\beta$-amino-penicillanic acid-1,1-dioxide used was 6.2 g (purity by HPLC=88%; 22 mmol) and 7.5 ml (67 mmol) of methanesulfonic acid were used instead of hydrobromic acid (7.46 ml 67.0 mmol). The isolated yield was 1.06 g.

EXAMPLE 32

The reaction was carried out as described in Example 31 but with $H_3BO_3$ (4.14 g 67 mmol) instead of methanesulfonic acid and the isolated yield was 3.65 g.

EXAMPLE 33

The reaction was carried out as described in Example 31, but with 7.5 ml (67 mmol) of phosphoric acid instead of methanesulfonic acid. The isolated yield was 5.98 g.

EXAMPLE 34

The reaction was carried out as described in Example 31 using 7.5 ml (67 mmol) of sulfuric acid instead of methanesulfonic acid and the isolated yield was 2.97 g.

EXAMPLE 35

The reaction was carried out as described in Example 12, but with 6.2 g (purity by HPLC=88% 22 mmol) of 6$\beta$-amino-penicillanic acid-1,1-dioxide and chloroform instead of dichloromethane as solvent. The isolated yield was 7.15 g.

EXAMPLE 36

The reaction was carried out as described in Example 35, using ethyl acetate instead of chloroform as the solvent. The isolated yield was 5.68 g which contained about 6% of 6$\alpha$-bromo-penicillanic acid-1,1-dioxide. The mother liquor after isolation of the product contained (through HPLC) 6.5% and 3.7% of 6,6-dibromo-penicillanic acid-1,1-dioxide and 6$\alpha$-bromo-penicillanic acid-1,1-dioxide, respectively from a total weight of 1.52 g after evaporation of the solvent.

EXAMPLE 37

The reaction was carried out as described in Example 35, using acetonitrile instead of chloroform as the solvent. The isolated yield was 7.15 g which contained about 4% of 6$\alpha$-bromo-penicillanic acid-1,1-dioxide (through HPLC).

EXAMPLE 38

The reaction was carried out as described in Example 35, using tetrahydrofuran instead of chloroform as the solvent. Furthermore, pure bromine was added to the reaction mixture at $-5°$ to 0° C. instead of a solution of bromine in the solvent. The isolated yield was 3.17 g which contained about 3.5% of 6$\alpha$-bromo-penicillanic acid-1,1-dioxide. The mother liquor after isolation of the product also contained 4.1% and 58% respectively of 6$\alpha$-bromo-penicillanic acid-1,1-dioxide and 6,6-dibromo-penicillanic acid-1,1-dioxide, respectively from a total weight of 1.58 g after evaporating the solvent. (purity determined through HPLC).

EXAMPLE 39

The reaction was carried out as described in Example 35, using nitromethane instead of chloroform as the solvent. The isolated yield was 5.75 g which contained about 1.2% of 6α-bromo-penicillanic acid-1,1-dioxide. The mother liquor after isolation of the product contained 1.3% and 41% respectively of 6α-bromo-penicillanic acid-1,1-dioxide and 6,6-dibromo-penicillanic acid-1,1-dioxide, respectively from a total weight of 1.44 g after evaporation of the solvent.

EXAMPLE 40

The reaction was carried out as described in Example 12, with 6.29 g (purity to HPLC=86.5% 21.62 mmol) of 6-amino-penicillanic acid-1,1-dioxide and 5.6 ml (98.9 mmol) of 96% ethanol instead of methanol. The isolated yield was 6.98 g.

EXAMPLE 41

The reaction was carried out as described in Example 12, but the amount of 6β-amino-penicillanic acid-1,1-dioxide used was 6.2 g (purity by HPLC=88% 22 mmol) and 9 ml(98.9 mmol) of n-butanol were used instead of methanol. The isolated yield was 6.84 g.

EXAMPLE 42

The reaction was carried out as described in Example 41, using 7.6 ml (98.9 mmol) of isopropanol instead of n-butanol. The isolated yield was 6.66 g.

EXAMPLE 43

The reaction was carried out as described in Example 41, using 9.13 ml (98.9 mmol) of isobutanol instead of n-butanol. and the isolated yield was 6.37 g.

EXAMPLE 44

The reaction was carried out as described in Example 41, using 10.3 ml (98.9 mmol) of cyclohexanol instead of n-butanol and the isolated yield was 5.4 g.

EXAMPLE 45

The reaction was carried out as described in Example 41, using 7.26 ml (98.9 mmol) of 1,2-propanediol instead of n-butanol and the isolated yield was 7.02 g.

Various modifications of the process of the invention may be made without departing from the spirit or scope thereof and it should be understood that the invention is intended to be limited only as defined in the appended claims.

What we claim is:

1. In a process for the preparation of 6,6-dibromo-penicillanic acid-1,1-dioxide comprising reacting 6β-amino-penicillanic acid-1,1-dioxide with a nitrosating agent in the presence of bromine and an inorganic acid or strong organic acid, the improvement comprising effecting the reaction in the presence of an alcohol.

2. The process of claim 1 wherein the alcohol is methanol.

3. The process of claim 2 wherein the amount of methanol is 1 to 10 equivalents.

4. The process of claim 3 using 2 to 6 equivalents of methanol.

5. The process of claim 4 using 4 equivalents of methanol.

6. The process of claim 1 wherein the nitrosating agent is an alkali metal nitrite.

7. The process of claim 1 wherein the nitrosating agent is sodium nitrite.

8. The process of claim 1 wherein the nitrosating agent is an alkane nitrite.

9. The process of claim 1 wherein the acid is hydrobromic acid.

10. The process of claim 1 wherein the reaction is performed in methylene chloride.

11. The process of claim 1 wherein the reaction is carried out at a temperature between −20° and 30° C.

12. The process of claim 1 wherein the temperature is between −10° and 15° C.

13. The process of claim 1 wherein the alcohol is an alkanol of 1 to 4 carbon atoms.

14. The process of claim 1 wherein the alcohol is an alkanediol of 1 to 4 carbon atoms.

* * * * *